(12) United States Patent
Nakano et al.

(10) Patent No.: US 10,045,727 B2
(45) Date of Patent: Aug. 14, 2018

(54) AROUSAL LEVEL DETERMINATION DEVICE AND COMPUTER-READABLE RECORDING MEDIUM

(71) Applicant: FUJITSU LIMITED, Kawasaki-shi, Kanagawa (JP)

(72) Inventors: Yasuhiko Nakano, Kawasaki (JP); Satoshi Sano, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 35 days.

(21) Appl. No.: 15/064,064

(22) Filed: Mar. 8, 2016

(65) Prior Publication Data

US 2016/0262683 A1 Sep. 15, 2016

(30) Foreign Application Priority Data

Mar. 9, 2015 (JP) .................. 2015-045955

(51) Int. Cl.
- A61B 5/02 (2006.01)
- A61B 5/04 (2006.01)
- A61B 5/18 (2006.01)
- A61B 5/024 (2006.01)
- A61B 5/00 (2006.01)
- A61B 5/16 (2006.01)

(52) U.S. Cl.
CPC .............. *A61B 5/18* (2013.01); *A61B 5/024* (2013.01); *A61B 5/165* (2013.01); *A61B 5/7257* (2013.01); *A61B 5/7282* (2013.01)

(58) Field of Classification Search
USPC ................................ 600/508–509
See application file for complete search history.

(56) References Cited

U.S. PATENT DOCUMENTS

| 2004/0243013 | A1 | 12/2004 | Kawachi et al. |
| 2008/0119994 | A1 | 5/2008 | Kameyama |
| 2011/0301433 | A1* | 12/2011 | Sadowsky ........ G06Q 30/0271 600/300 |
| 2012/0078122 | A1* | 3/2012 | Yokoyama ......... A61B 5/0245 600/484 |

FOREIGN PATENT DOCUMENTS

| JP | H08-153288 | 6/1996 |
| JP | 2004-350773 | 12/2004 |
| JP | 2008-126818 | 6/2008 |
| JP | 2011-248746 | 12/2011 |

\* cited by examiner

*Primary Examiner* — Nicole F Johnson
(74) *Attorney, Agent, or Firm* — Fujitsu Patent Center (57) ABSTRACT

A non-transitory computer-readable recording medium stores a program that causes a computer to execute a process including: first setting an arousal section including from a time point when a subject has got on a vehicle to a time point when a predetermined time has elapsed thereafter; determining whether an arousal level of the subject has moved toward arousal in a section which is temporally later than the arousal section, based on a biosignal detected from the subject; when the arousal level has moved toward arousal in the section which is temporally later than the arousal section, updating the arousal section with a section in which the arousal level has moved toward arousal; and second setting a threshold value for determining whether the subject is in an arousal state, based on a statistical value of the subject's arousal levels corresponding to the updated arousal section.

6 Claims, 7 Drawing Sheets

| START TIME | ENDING TIME | MAXIMUM AROUSAL LEVEL |
|---|---|---|
| tx | ty | AROUSAL LEVEL X |

AROUSAL LEVEL DETERMINATION DEVICE AND COMPUTER-READABLE RECORDING MEDIUM

CROSS-REFERENCE TO RELATED APPLICATION

This application is based upon and claims the benefit of priority of the prior Japanese Patent Application No. 2015-045955, filed on Mar. 9, 2015, the entire contents of which are incorporated herein by reference.

FIELD

The embodiments discussed herein are related to an arousal level determination program and the like.

BACKGROUND

Although the total number of traffic accidents has decreased year after year, the number of traffic accidents caused by human error has not much decreased. One factor of traffic accidents caused by human error is sleepiness while driving. Accordingly, a technique is demanded which prevents traffic accidents from occurring by issuing a warning to drivers based on their arousal levels while driving.

For example, as Related Art 1 for determining arousal levels, there is a technique using a low frequency (LF)/high frequency (HF) index. In a case where a heartbeat signal of a driver is converted into a frequency and a relationship between the frequency and a spectral density is calculated, LF is a value obtained by integrating spectral densities in a low frequency band. HF is a value obtained by integrating spectral densities in a high frequency band. In Related Art 1, sleepiness is determined based on the ratio between LF and HF. For example, when the ratio between LF and HF is 7:3, the driver is determined to be in an arousal state, and when the ratio between LF and HF is 3:7, the driver is determined to be in a sleepy state.

However, in Related Art 1, a preset criterion for determining arousal levels, which is common to drivers, is used, and therefore, it is difficult to deal with individual differences in arousal levels of respective drivers.

In contrast, in Related Art 2, which is another technique for determining arousal levels, a technique is disclosed in which a driver is determined to be in an arousal state immediately after the driver starts driving, and a peak frequency of a spectral signal obtained predetermined hours after the start of driving is used as a frequency at a peak during arousal of the driver.

Patent Document 1: Japanese Laid-open Patent Publication No. 08-153288
Patent Document 2: Japanese Laid-open Patent Publication No. 2008-126818
Patent Document 3: Japanese Laid-open Patent Publication No. 2011-248746
Patent Document 4: Japanese Laid-open Patent Publication No. 2004-350773

However, there is a problem in the related arts described above that it is difficult to set, for each person, a threshold value for determining arousal levels.

In Related Art 2, although a driver is determined to be in an arousal state immediately after the driver starts driving, in some cases, drivers are not in an arousal state even immediately after they start driving. In addition, there may be a case where a peak frequency of a spectral signal, which is obtained predetermined hours after the driver starts driving, is not a frequency at a peak during arousal of the driver.

SUMMARY

According to an aspect of the embodiments, a non-transitory computer-readable recording medium stores an arousal level determination program that causes a computer to execute a process including: first setting an arousal section including from a time point when a subject has got on a vehicle to a time point when a predetermined time has elapsed thereafter; determining whether an arousal level of the subject has moved toward arousal in a section which is temporally later than the arousal section, based on a biosignal detected from the subject; when the arousal level of the subject has moved toward arousal in the section which is temporally later than the arousal section, updating the arousal section with a section in which the arousal level of the subject has moved toward arousal; and second setting a threshold value for determining whether the subject is in an arousal state, based on a statistical value of the subject's arousal levels corresponding to the updated arousal section.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Preferred embodiments will be explained with reference to accompanying drawings. The present invention is not limited by the embodiments.

Figures 1, 2:
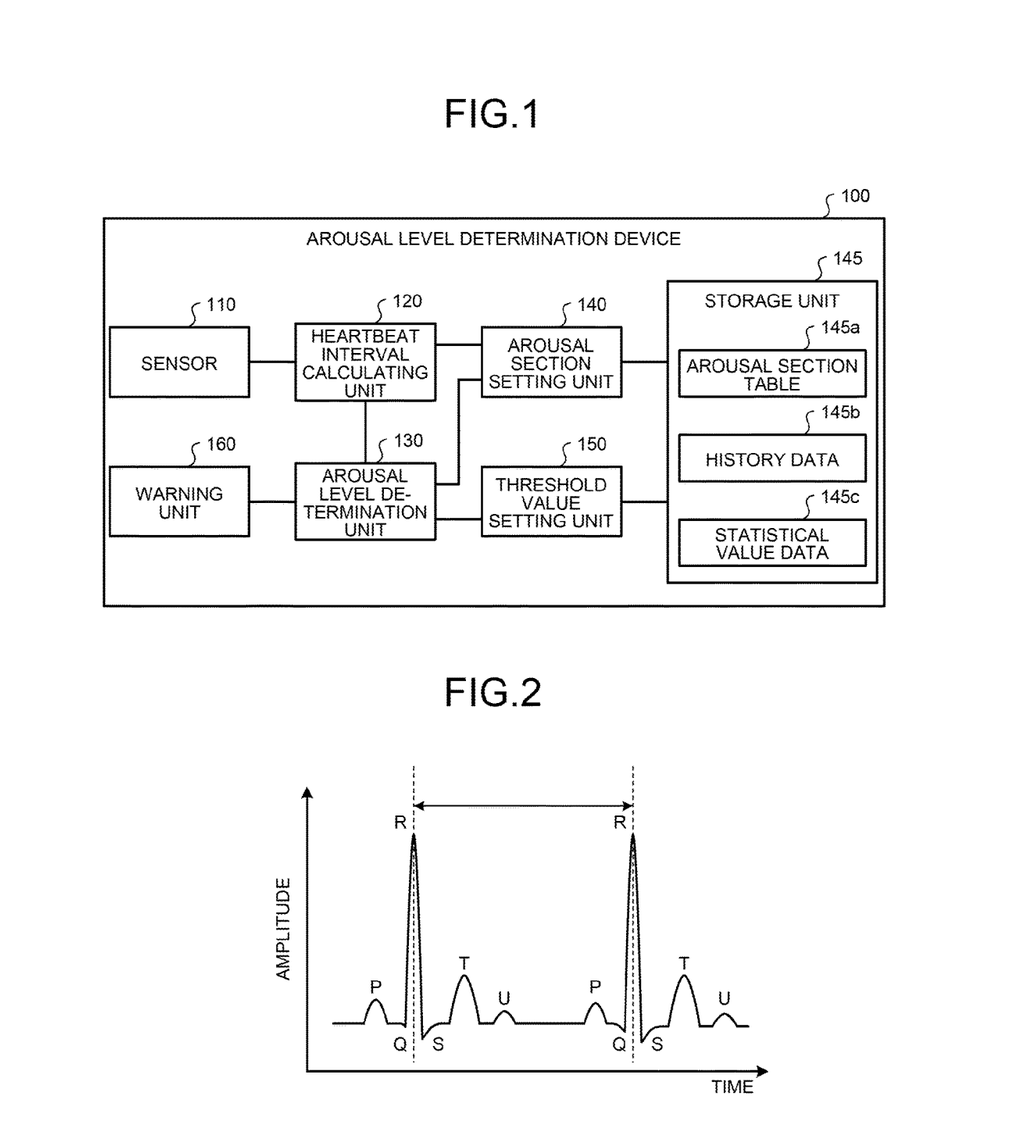
FIG. 1 is a functional block diagram illustrating a configuration of an arousal level determination device according to an embodiment.
FIG. 2 is a diagram illustrating an example of heartbeat signal data.

FIG. 1 a functional block diagram illustrating a configuration of the arousal level determination device according to the embodiment. As illustrated in FIG. 1, an arousal level determination device 100 includes a sensor 110, a heartbeat interval calculating unit 120, an arousal level determination unit 130, an arousal section setting unit 140, a storage unit 145, a threshold value setting unit 150, and a warning unit 160.

The sensor 110 is a sensor which detects a heartbeat signal of a subject. The subject corresponds to, for example, a driver of a vehicle. For example, the sensor 110 is installed on a steering wheel of a vehicle. In the present embodiment, a case of detecting a heartbeat signal is described as an example, but the sensor 110 may detect a pulse signal of a subject. The heartbeat signal and the pulse signal are examples of biosignals. The sensor 110 outputs data of heartbeat signals to the heartbeat interval calculating unit 120. In the following description, data of heartbeat signals is described as heartbeat signal data.

FIG. 2 is a diagram illustrating an example of heartbeat signal data. As illustrated in FIG. 2, heartbeat signal data have waveforms referred to as P, Q, R, S and T waves. For example, in FIG. 2, the horizontal axis indicates time, and the vertical axis indicates amplitudes of the heartbeat signal.

The heartbeat interval calculating unit 120 is a processing unit which detects an amplitude peak of the heartbeat signal based on the heartbeat signal data, and detects an interval of the timing of detection. The interval of the timing, at which the amplitude peak of the heartbeat signal is detected, is described as a heartbeat interval. With reference to FIG. 2, a process performed by the heartbeat interval calculating unit 120 is described. As illustrated in FIG. 2, the heartbeat interval calculating unit 120 detects a point R at which the amplitude of the heartbeat signal is equal to or more than a threshold value, that is, an amplitude peak, and detects intervals between each point R thus detected, as amplitude intervals. The heartbeat interval calculating unit 120 outputs data of detected heartbeat intervals to the arousal level determination unit 130 and the arousal section setting unit 140. In the following description, data of heartbeat intervals is described as heartbeat interval data.

The arousal level determination unit 130 is a processing unit which determines an arousal level of a subject at each time point based on the heartbeat interval data. For example, the arousal level determination unit 130 performs a process for calculating spectral densities corresponding to heartbeat intervals, and determines arousal levels based on the maximum value of the spectral densities and a frequency corresponding to the maximum value of the spectral densities. For example, the higher the arousal level, the less sleepy the subject feels, and the lower the arousal level, the more sleepy the subject feels. The arousal level determination unit 130 outputs arousal level information to the arousal section setting unit 140. Furthermore, the arousal level determination unit 130 compares the arousal level and the threshold value TH to determine whether the subject feels sleepy, and outputs the determination result to the warning unit 160. The threshold value TH, which is used by the arousal level determination unit 130, is set by the threshold value setting unit 150 described later.

Hereinbelow, an example of the process performed by the arousal level determination unit 130 to calculate spectral densities corresponding to heartbeat intervals is described. The arousal level determination unit 130 creates data of heartbeat intervals which vary with time based on the heartbeat interval data. In the following description, data of heartbeat intervals which vary with time is described as heartbeat interval variation data.

Figure 3:
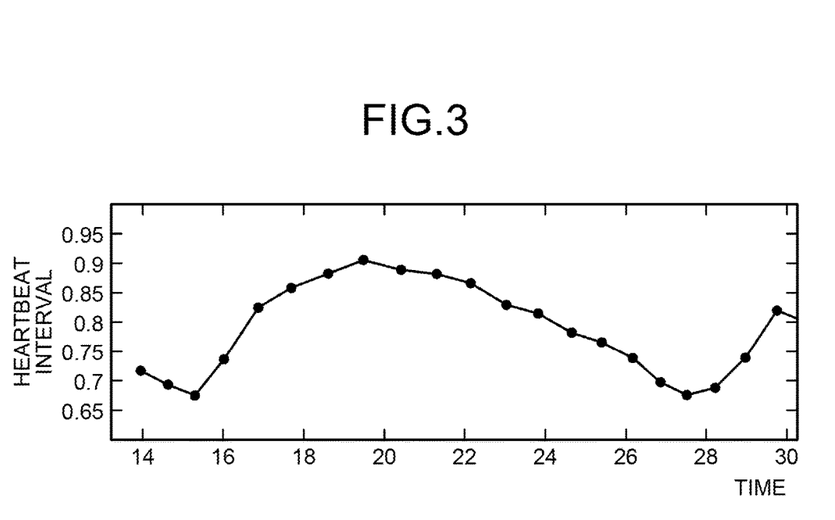
FIG. 3 is a diagram illustrating an example of heartbeat interval variation data.

FIG. 3 is a diagram illustrating an example of heartbeat interval variation data. In FIG. 3, the vertical axis indicates heartbeat intervals, and the horizontal axis indicates time. As illustrated in FIG. 3, the heartbeat interval varies with time.

Figure 4:
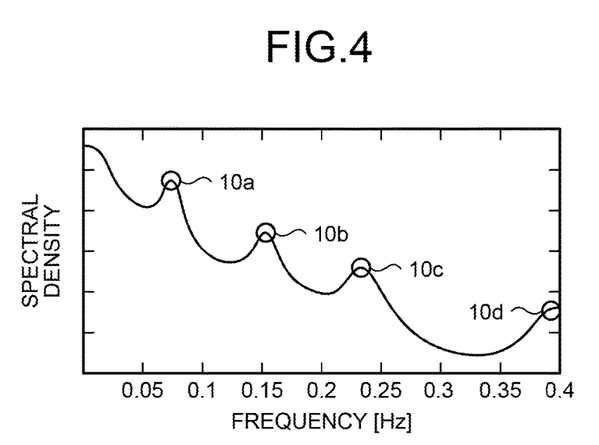
FIG. 4 is a diagram illustrating a relationship between frequencies and spectral densities.

The arousal level determination unit 130 calculates a relationship between frequencies and spectral densities based on the heartbeat interval variation data. FIG. 4 is a diagram illustrating the relationship between frequencies and spectral densities. In FIG. 4, the vertical axis indicates spectral densities, and the horizontal axis indicates frequencies. In the example illustrated in FIG. 4, there are maximum spectral densities at points 10a, 10b, 10c and 10d. In the following description, data which illustrates the relationship between spectral densities and frequencies is described as spectral density data.

When the arousal level determination unit 130 calculates the relationship between spectral densities and frequencies, any method may be used. Spectral densities can be calculated with an autoregressive (AR) model. As disclosed, for example, in Non-Patent Document (SATO Shunsuke, KIKKAWA Sho and KIRYU Toru, *Basics of Biosignal Processing*, Corona Publishing Co., Ltd.), the AR model is a model which indicates a state at a certain time point as a linear sum of previous time series data, and has a characteristic that clear maximum points can be obtained even when the amount of data is small in comparison to the case of using Fourier transform. The arousal level determination unit 130 may calculate the relationship between spectral densities and frequencies by Fourier transform.

A p-th order AR model of time series x(s) can be represented by Formula (1), by using an AR coefficient a(m) which is a weight to the previous values and an error term e(s). In Formula (1), e(s) is ideally a white noise.

$$x(s) = \sum_{m=1}^{P} a(m)x(s-m) + e(s) \qquad (1)$$

When defining p as an identification order, $f_s$ as a sampling frequency, $\varepsilon_p$ as an identification error, and $$\hat{a}_P(k) \qquad (2)$$

as a k-th order AR coefficient, spectral density $P_{AR}$ (f) is represented by Formula (3). The arousal level determination unit 130 calculates spectral density data based on Formula (3) and the heartbeat interval variation data.

$$P_{AR}(f) = \frac{1}{f_S} \frac{\varepsilon_P}{\left| 1 + \sum_{k=1}^{P} \hat{a}_P(k) e^{\frac{-2\pi jkf}{f_k}} \right|^2} \qquad (3)$$

Subsequently, an example of a process performed by the arousal level determination unit 130 to determine sleepiness levels based on the maximum value of the spectral densities and a frequency corresponding to the maximum value of the spectral densities. In the following description, the maximum value of the spectral densities is described as the maximum spectral density. Furthermore, the frequency corresponding to the maximum spectral density is described as the maximum frequency.

The arousal level determination unit 130 calculates, as the maximum frequency, a frequency f which satisfies the relationship of Formula (4). The arousal level determination unit 130 obtains the maximum spectral density by substituting the maximum frequency into Formula (3).

$$\frac{dP_{AR}(f)}{df} = 0 \qquad (4)$$

The arousal level determination unit 130 selects any one of the maximum spectral densities based on the spectral density data. For example, in FIG. 4, the arousal level determination unit 130 selects any one of the maximum spectral densities 10a to 10d, and focuses on variation with time of the selected maximum spectral density and the maximum frequency corresponding to the maximum spectral density.

For example, the arousal level determination unit 130 plots, on a graph, the relationship between the focused maximum spectral density and the maximum frequency corresponding to the maximum spectral density. A point on the graph specified by the maximum spectral density and the maximum frequency is described as a feature point. The arousal level determination unit 130 determines an arousal level of a subject based on the position of the feature point on the graph.

Figure 5:
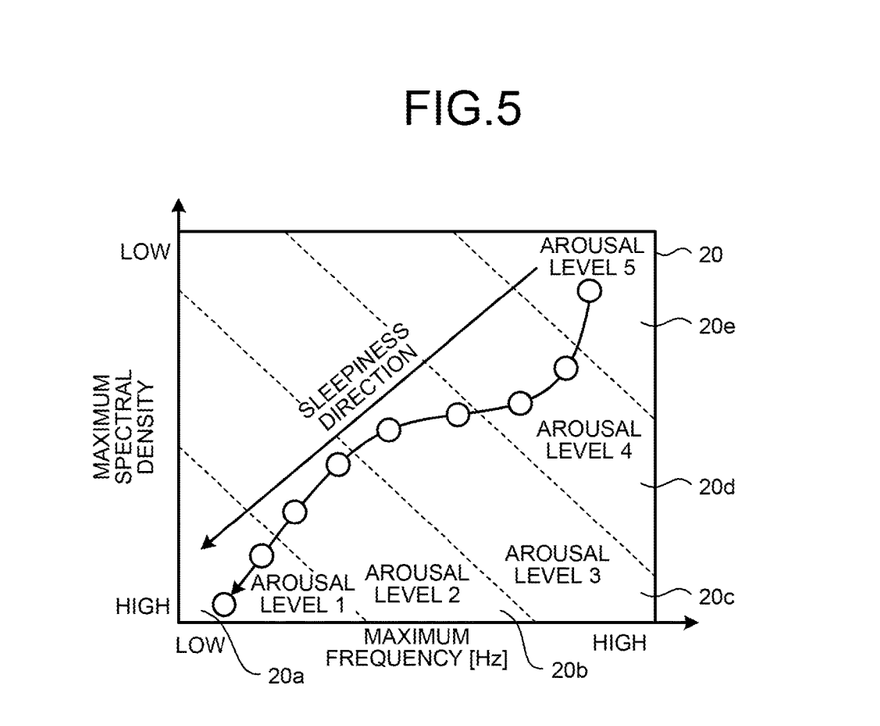
FIG. 5 is a diagram for explaining an arousal level determination process.

FIG. 5 is a diagram for explaining an arousal level determination process. The vertical axis of a graph 20 illustrated in the figure corresponds to the maximum spectral density. In the graph 20, the maximum spectral density decreases upward from bottom. The horizontal axis of the graph 20 corresponds to the maximum frequency. In the graph 20, the maximum frequency increases from left toward right. When the maximum frequency decreases and the maximum spectral density increases, the subject feels sleepy and the arousal level of the subject lowers. In contrast, when the maximum frequency increases and the maximum spectral density decreases, the subject feels less sleepy and the arousal level of the subject increases. In other words, when a feature point has moved in an upper right direction from the lower left, the arousal level of the subject may be considered to have moved toward arousal.

For example, the arousal level determination unit 130 determines an arousal level of the subject as "arousal level 1" when the position of the feature point is included in an area 20a. The arousal level determination unit 130 determines an arousal level of the subject as "arousal level 2" when the position of the feature point is included in an area 20b. The arousal level determination unit 130 determines an arousal level of the subject as "arousal level 3" when the position of the feature point is included in an area 20c. The arousal level determination unit 130 determines an arousal level of the subject as "arousal level 4" when the position of the feature point is included in an area 20d. The arousal level determination unit 130 determines an arousal level of the subject as "arousal level 5" when the position of the feature point is included in an area 20e.

In the graph illustrated in FIG. 5, as an example, the area of the graph 20 is divided into 20a to 20e, and the arousal levels of the subject are classified into any one of arousal level 1 to arousal level 5. However, there is no limitation thereto. For example, the area of the graph 20 may be divided into smaller areas, and the arousal levels of the subject may be classified into finer categories.

The arousal level determination unit 130 compares the arousal level and the threshold value TH, and determines whether the arousal level is below the threshold value TH. When the arousal level is below the threshold value TH, the arousal level determination unit 130 outputs to the warning unit 160 the fact that the arousal level of the subject is below the threshold value TH.

The arousal section setting unit 140 is a processing unit which sets an arousal section indicating a section in which a subject is in an arousal state. The arousal section setting unit 140 registers information of the arousal section with an arousal section table 140a of the storage unit 145. The arousal state is a state where an arousal level of a subject is equal to or higher than a predetermined value. The predetermined value may be the same value as the threshold value TH. In addition, the arousal section setting unit 140 associates the arousal level and the time received from the arousal level determination unit 130 with each other, and registers the arousal level and the time with history data 145b of the storage unit 145.

Figure 6:
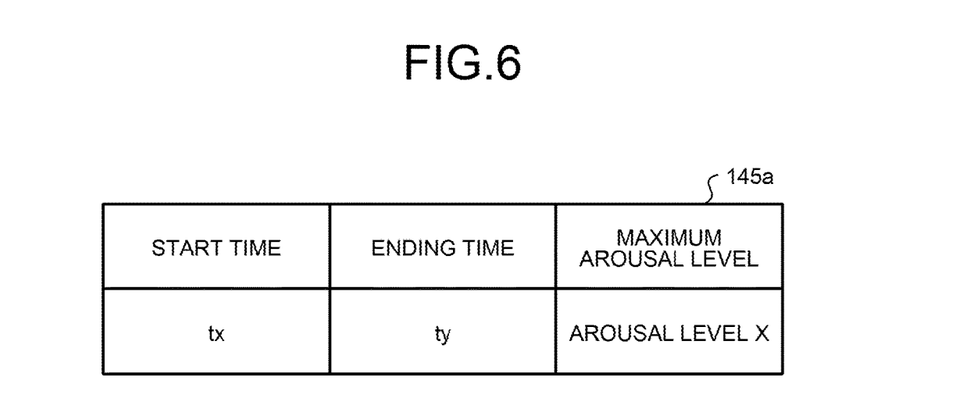
FIG. 6 is a diagram illustrating an example of a data structure of an arousal section table.

FIG. 6 is a diagram illustrating an example of a data structure of an arousal section table. As illustrated in FIG. 6, an arousal section table 145a associates start time, ending time, and the maximum arousal level with one another. Of these, the start time corresponds to time when the arousal section starts, and the ending time corresponds to time when the arousal section ends. The maximum arousal level corresponds to an arousal level which is maximum among arousal levels in arousal sections included in from the start time to the ending time.

Figure 7:
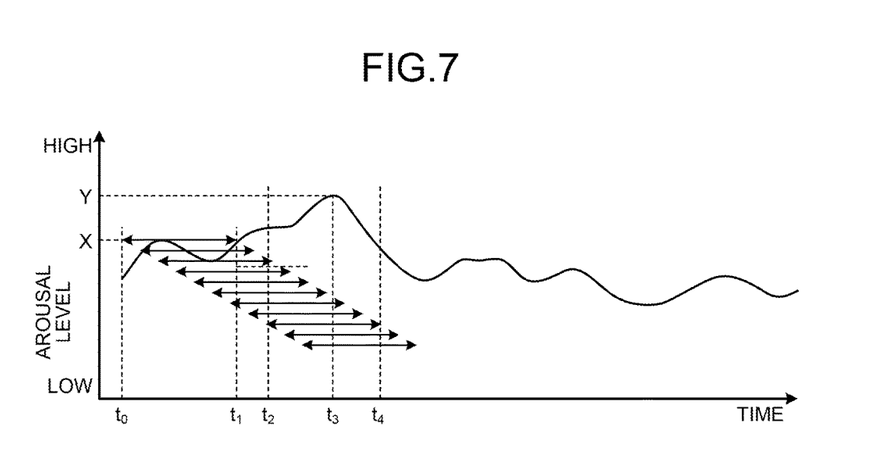
FIG. 7 is a diagram illustrating a relationship between arousal levels and time.

An example of the process performed by the arousal section setting unit 140 to set an arousal section is described. FIG. 7 is a diagram illustrating a relationship between arousal levels and time. In FIG. 7, the vertical axis corresponds to arousal levels, and the horizontal axis corresponds to time. The arousal section setting unit 140 sets a section including time $t_0$, which is a time point when a subject gets on a vehicle, to time $t_1$, as an initial arousal section. For example, when a window size of an arousal section is set at 10 minutes, time from $t_0$ to $t_1$ is 10 minutes.

The arousal section setting unit 140 may determine any time point as time $t_0$. For example, the arousal section setting unit 140 may determine, as time $t_0$, the time point when the sensor 110 starts detecting the heartbeat signal of the subject, or may receive information from the subject indicating that the subject gets on a vehicle. Furthermore, the window size of the arousal section has been set to 10 minutes, but not limited thereto. The window size may be set to eight minutes or five minutes.

After determining the arousal section, the arousal section setting unit 140 associates start time, ending time, and the maximum arousal level of the arousal section with one another, and registers the start time, the ending time, and the maximum arousal level with the arousal section table 145a.

The arousal section setting unit 140 monitors the arousal level output from the arousal level determination unit 130, compares the arousal level with the maximum arousal level registered with the arousal section table 145a, and determines whether the arousal level of the subject has moved toward arousal. The arousal section setting unit 140 updates information of the arousal section table 145a, when the arousal level of the subject has moved toward arousal. For example, the arousal section setting unit 140 determines that the arousal level of the subject has moved toward arousal when the arousal level output from the arousal level determination unit 130 has exceeded the maximum arousal level of the arousal section table 145a.

For example, in FIG. 7, the present arousal section is set at time $t_0$ to time $t_1$, and the maximum arousal level is set at an arousal level X. When an arousal level Y, which is higher than the arousal level X, is detected in time $t_3$, the arousal section setting unit 140 updates the arousal section including times $t_2$ to $t_4$ as a new arousal section. The arousal section setting unit 140 updates the arousal section by updating a record of the arousal section table 145a with start time "$t_2$", ending time "$t_4$", and the maximum arousal level "arousal level Y". The start time and the ending time of the arousal section to be updated may be set arbitrarily as long as the window size thereof includes the maximum arousal level Y.

When updating the arousal section, the arousal section setting unit 140 determines whether to continue an update process or inhibit the update process, based on the heartbeat intervals output from the heartbeat interval calculating unit 120.

For example, the arousal section setting unit 140 calculates an average value of heartbeat intervals in a predetermined section. In the following description, the average value of heartbeat intervals is described as an average heartbeat interval value. The arousal section setting unit 140 calculates a difference value between a heartbeat interval and the average heartbeat interval value for each time point and determines whether there is a time point at which the calculated difference value exceeds the noise threshold value. Then, in the case where an arousal section to be potentially updated includes a time point at which the difference value exceeds the noise threshold value, the arousal section setting unit 140 inhibits the process for updating the arousal section with the arousal section to be potentially updated. In contrast, in the case where an arousal section to be potentially updated does not include a time point at which the difference value exceeds the noise threshold value, the arousal section setting unit 140 updates the arousal section with the arousal section to be potentially updated.

The arousal section setting unit 140 may set any noise threshold value. For example, the arousal section setting unit 140 uses a value corresponding to 20% of the average heartbeat interval value as the noise threshold value. Furthermore, even in the case where the difference value and the minimum threshold value are compared and the difference value is smaller than the minimum threshold value, the arousal section setting unit 140 may inhibit the process for updating the arousal section with the arousal section to be potentially updated. The minimum threshold value is a value smaller than the noise threshold value and appropriately set by a manager. When the difference value is smaller than the minimum threshold value, it means that there is less variation in the heartbeat intervals. In the above, the case where the arousal section setting unit 140 calculates an average value of heartbeat intervals has been described. However, a median value may be used instead of the average value. In that case, the arousal section setting unit 140 calculates a difference value between a heartbeat interval and the median value of heartbeat intervals for each time point and performs the determination described above.

Figure 8:
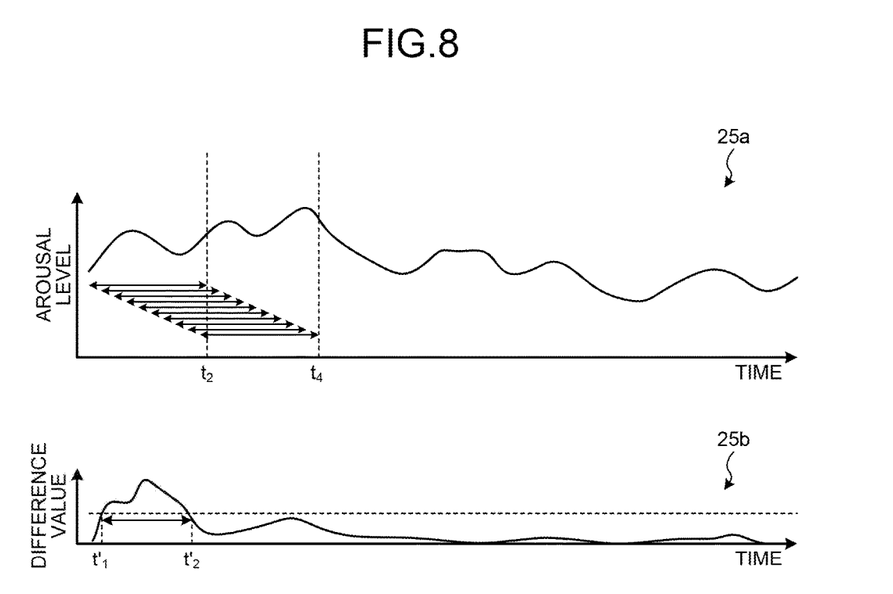
FIG. 8 is a diagram for explaining a process performed by an arousal section setting unit.

FIG. 8 is a diagram for explaining a process performed by an arousal section setting unit. In FIG. 8, a graph 25a indicates a relationship between time and arousal levels. A graph 25b indicates a relationship between time and difference values. In the graph 25a, the vertical axis corresponds to arousal levels, and the horizontal axis corresponds to time. In the graph 25b, the vertical axis corresponds to difference values, and the horizontal axis corresponds to time.

For example, it is assumed that the arousal section setting unit 140 determines a section including time $t_2$ to time $t_4$, as an arousal section to be updated. It is further assumed that the arousal section setting unit 140 determines that the difference value has exceeded the noise threshold value in a section including time $t'_1$ to time $t'_2$. In that case, since the arousal section does not include a time point at which the difference value exceeds the noise threshold value, the arousal section setting unit 140 updates the record of the arousal section table 145a with information of the arousal section to be updated.

The arousal section setting unit 140 may search for an arousal section satisfying a condition 1 and a condition 2 below and update the record of the arousal section table 145a with the arousal section found.

Condition 1: an arousal section to be updated does not include a time point at which the difference value exceeds the noise threshold value.

Condition 2: an arousal section to be updated includes the maximum arousal level higher than the maximum arousal level stored in the arousal section table 145a.

Return to the description of FIG. 1. The storage unit 145 includes the arousal section table 145a, the history data 145b and statistical value data 145c. The storage unit 145 corresponds, for example, to a storage device including a semiconductor memory device such as a random access memory (RAM), a read only memory (ROM), and a flash memory.

As described with reference to FIG. 6, the arousal section table 145a is a table which retains information of the arousal section. The history data 145b is a table which retains information of the arousal level at each time point. The statistical value data 145c is a table which retains information of statistical values calculated by the threshold value setting unit 150 described later. The information of the statistical values corresponds to an average value of the arousal levels and a standard deviation of the arousal levels.

The threshold value setting unit 150 is a processing unit which calculates a statistical value of arousal levels included in an arousal section, and calculates a threshold value TH. The threshold value TH is used by the arousal level determination unit 130 described above. The statistical value of the arousal levels corresponds to the average value and the standard deviation of the arousal levels included in the arousal section. The threshold value setting unit 150 specifies the arousal section based on the arousal section table 145a. Furthermore, the threshold value setting unit 150 acquires information of the arousal levels included in the arousal section from the history data 145b.

The threshold value setting unit 150 calculates the threshold value TH according to Formula (5). In Formula (5), an average arousal value T is an average value of the arousal levels included in the arousal section. The standard deviation σ is a standard deviation of the arousal levels included in the arousal section.

Threshold value $TH$=average arousal value $T$−3× standard deviation σ (5)

The threshold value setting unit 150 calculates the average arousal value T using Formula (6). In Formula (6), $x_i$ corresponds to an arousal level at a certain time point included in the arousal section. N corresponds to the number of the arousal levels included in the arousal section.

$$T = \frac{1}{N}\sum_{i=1}^{N} x_i \qquad (6)$$

The threshold value setting unit 150 calculates the standard deviation σ using Formula (7). In Formula (7), $x_i$ corresponds to an arousal level at a certain time point included in the arousal section. N corresponds to the number of the arousal levels included in the arousal section.

$$\sigma^2 = \frac{1}{N} \sum_{i=1}^{N} (x_i - T)^2 \qquad (7)$$

The threshold value setting unit 150 may separately average the average arousal values T and the standard deviations σ to be sequentially calculated, and apply the averaged values to Formula (5) to calculate the threshold value TH.

In the case where the threshold value setting unit 150 calculates the average arousal value T and the standard deviation σ at the first time, the threshold value setting unit 150 associates the average arousal value T and the standard deviation σ with each other and registers the average arousal value T and the standard deviation σ with the statistical value data 145c of the storage unit 145.

In the case where the threshold value setting unit 150 calculates the average arousal value T at the second time or thereafter, the threshold value setting unit 150 calculates the average value of the average arousal value T registered with the statistical value data 145c and the average arousal value T obtained by current calculation, and the calculated average value is used as the average arousal value T. The threshold value setting unit 150 updates the average arousal value T of the statistical value data 145c with the calculated average value.

In the case where the threshold value setting unit 150 calculates the standard deviation σ at the second time or thereafter, the threshold value setting unit 150 calculates the average value of the standard deviation σ registered with the statistical value data 145c and the standard deviation σ obtained by current calculation, and the calculated average value is used as the standard deviation σ. The threshold value setting unit 150 updates the standard deviation σ of the statistical value data 145c with the calculated average value.

Figure 9:
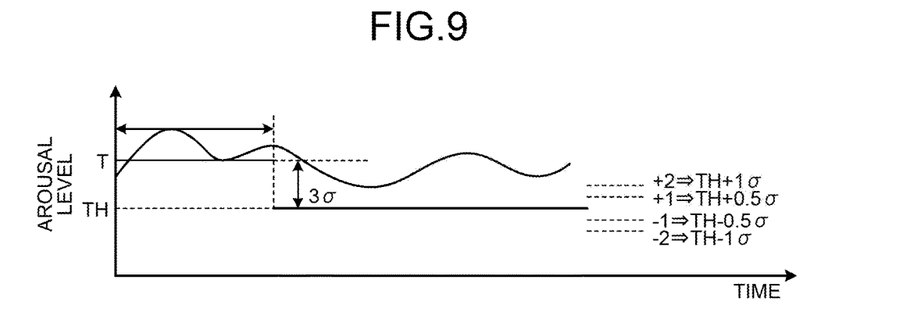
FIG. 9 is a diagram illustrating an example of a threshold value TH set by a threshold value setting unit.

FIG. 9 is a diagram illustrating an example of a threshold value TH set by a threshold value setting unit. In FIG. 9, the vertical axis corresponds to arousal levels, and the horizontal axis corresponds to time. As illustrated in FIG. 9, the threshold value TH is set at a position 3σ lower than the average arousal value T.

Figure 10:
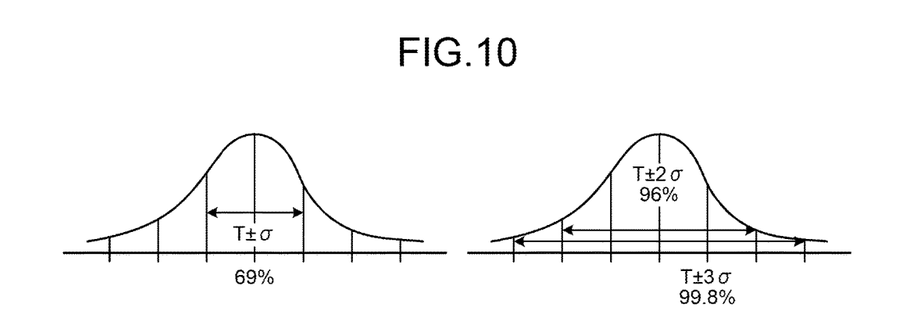
FIG. 10 is a diagram illustrating normal distribution of average arousal values T and a standard deviation σ.

FIG. 10 is a diagram illustrating normal distribution of average arousal values T and a standard deviation σ. As illustrated in FIG. 10, for example, in a range of average arousal T±σ, the arousal levels of 69% of the total subjects are included. In a range of average arousal T±2σ, the arousal levels of 96% of the total subjects can be obtained. In a range of average arousal T±3σ, the arousal levels of 99.8% of the total subjects are included.

As illustrated in FIG. 10, in the range of average arousal T±3σ, the arousal levels of 99.8% of the total subjects are included. Accordingly, by calculating the threshold value TH using Formula (5), it is possible to determine whether a subject is in an arousal state with respect to almost all subjects.

The threshold value setting unit 150 may correct the threshold value TH in accordance with information input from an input device not illustrated. For example, the threshold value setting unit 150 updates the threshold value TH using Formula (8) or Formula (9) in the case where the threshold value setting unit 150 receives instruction from the input device to increase the threshold value.

Updated threshold value TH=threshold value TH+0.5σ  (8)

Updated threshold value TH=threshold value TH+1σ  (9)

Furthermore, the threshold value setting unit 150 updates the threshold value TH using Formula (10) or Formula (11) in the case where the threshold value setting unit 150 receives instruction from the input device to decrease the threshold value.

Updated threshold value TH=threshold value TH−0.5σ  (10)

Updated threshold value TH=threshold value TH−1σ  (11)

The warning unit 160 is a processing unit which receives a determination result from the arousal level determination unit 130 and issues a warning in accordance with the determination result. Specifically, the warning unit 160 issues a warning to a subject upon receiving information indicating that the arousal level of the subject has dropped below the threshold value TH. The warning unit 160 may issue an audio warning, or may issue a video warning using a display installed in the vehicle.

Figure 11:
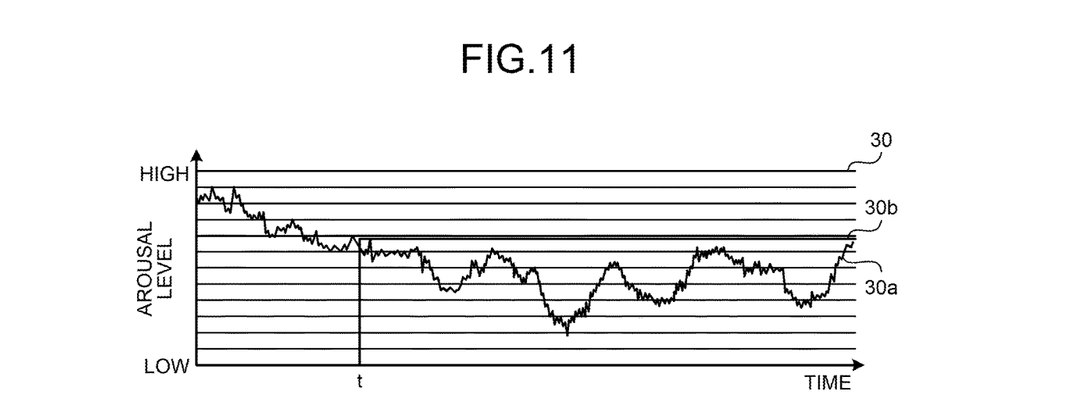
FIG. 11 is a diagram illustrating an example of timing for issuing a warning by a warning unit.

FIG. 11 is a diagram illustrating an example of timing for issuing a warning by the warning unit. In a graph 30 of FIG. 11, the vertical axis corresponds to arousal levels, and the horizontal axis corresponds to time. A line segment 30a in the graph 30 indicates the arousal level at each time point. A line segment 30b in the graph 30 corresponds to the threshold value TH. For example, at time t, the arousal level is below the threshold value TH. Accordingly, the warning unit 160 issues a warning to the subject.

Figure 12:
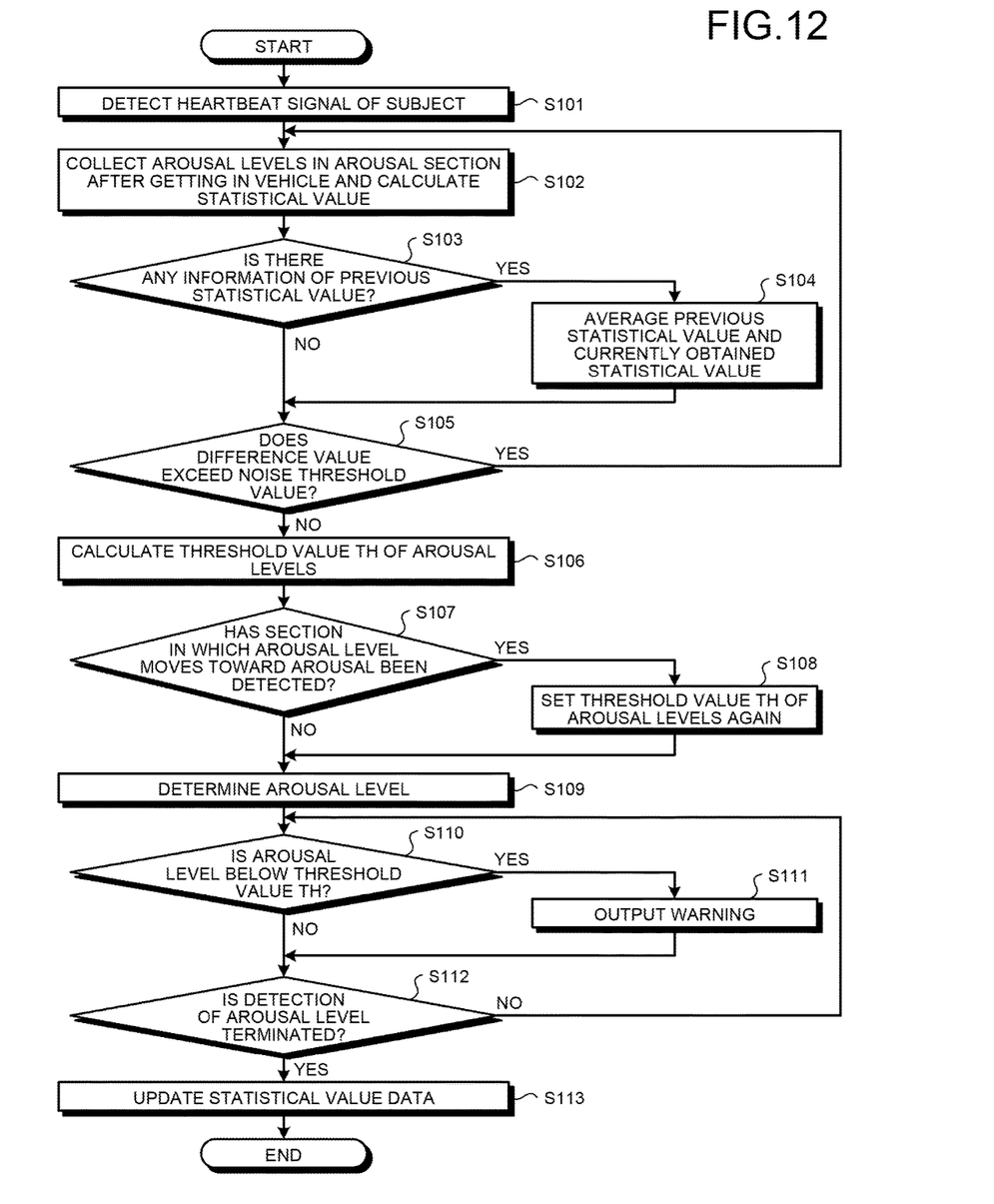
FIG. 12 is a flowchart illustrating a processing procedure performed by the arousal level determination device according to the embodiment.

Next, a processing procedure performed by the arousal level determination device 100 according to the embodiment is described. FIG. 12 is a flowchart illustrating a processing procedure performed by the arousal level determination device according to the embodiment. As illustrated in FIG. 12, the sensor 110 of the arousal level determination device 100 detects a heartbeat signal of a subject (Step S101). The threshold value setting unit 150 of the arousal level determination device 100 collects arousal levels in an arousal section after getting in the vehicle, and calculates a statistical value (Step S102).

The threshold value setting unit 150 determines whether there is information of a previous statistical value (Step S103). When there is no information of a previous statistical value (NO at Step S103), the threshold value setting unit 150 moves on to Step S105.

On the other hand, when there is information of a previous statistical value (YES at Step S103), the threshold value setting unit 150 averages the previous statistical value and the currently obtained statistical value (Step S104), and moves on to Step S105.

The arousal section setting unit 140 determines whether a difference value exceeds a noise threshold value (Step S105). When the difference value exceeds the noise threshold value (YES at Step S105), the arousal level determination device 100 moves on to Step S102.

On the other hand, when the difference value does not exceed the noise threshold value (NO at Step S105), the threshold value setting unit 150 of the arousal level determination device 100 calculates a threshold value TH of the arousal levels (Step S106).

The arousal section setting unit 140 determines whether a section has been detected in which the arousal level moves toward arousal (Step S107). When the section has not been detected in which the arousal level moves toward arousal (NO at Step S107), the arousal section setting unit 140 moves on to Step S109.

In the case where the section has been detected in which the arousal level moves toward arousal (YES at Step S107), the arousal section setting unit 140 sets the threshold value TH of the arousal levels again (Step S108) and moves on to Step S109.

The arousal level determination unit 130 of the arousal level determination device 100 determines an arousal level (Step S109). The arousal level determination unit 130 determines whether the arousal level is below the threshold value TH (Step S110). When the arousal level is not below the threshold value (NO at Step S110), the arousal level determination unit 130 moves on to Step S112.

On the other hand, when the arousal level is below the threshold value (YES at Step S110), the warning unit 160 of the arousal level determination device 100 outputs a warning (Step S111), and moves on to Step S112.

The arousal level determination device 100 determines whether the detection of the arousal levels is terminated (Step S112). When the detection of the arousal levels is not terminated (NO at Step S112), the arousal level determination unit 130 moves on to Step S110. When the detection of the arousal levels is terminated (YES at Step S112), the arousal section setting unit 140 updates the statistical value data 145*c* (Step S113).

Next, an advantageous effect of the arousal level determination device 100 according to the embodiment is described. The arousal level determination device 100 specifies, as an arousal section, a section in which a subject's arousal level has moved toward arousal in comparison to the subject's arousal level in a section immediately after the subject has got on the vehicle. The arousal level determination device 100 calculates a statistical value of the arousal levels included in the specified arousal section, and sets a threshold value TH for determining the arousal state of the subject based on the calculated statistical value. Accordingly, with the arousal level determination device 100, it is possible to set a threshold value TH unique to the subject based on the arousal section unique to each person. Furthermore, by doing so, it is possible to determine the arousal state of the subject.

The arousal level determination device 100 calculates a difference value between a heartbeat interval at each time point and an average heartbeat interval value, and determines whether there is a time point at which the calculated difference value exceeds the noise threshold value. Then, in the case where an arousal section to be potentially updated includes a time point at which the difference value exceeds the noise threshold value, the arousal level determination device 100 inhibits the process for updating the arousal section with the arousal section to be potentially updated. Consequently, with the arousal level determination device 100, it is possible to eliminate the effect of disturbance such as rubbing against the sensor 110 caused by movement of the subject or the like, on the threshold value TH.

The arousal level determination device 100 calculates an average value and a standard deviation of the arousal levels included in an arousal section, and sets a threshold value TH based on the calculated average arousal value and standard deviation. For example, when the arousal level determination device 100 sets, as the threshold value TH, a value obtained by subtracting 3σ from the average arousal value T, it is possible to set a threshold value TH with which almost all subjects' arousal states can be determined, in accordance with a concept of normal distribution.

Figure 13:
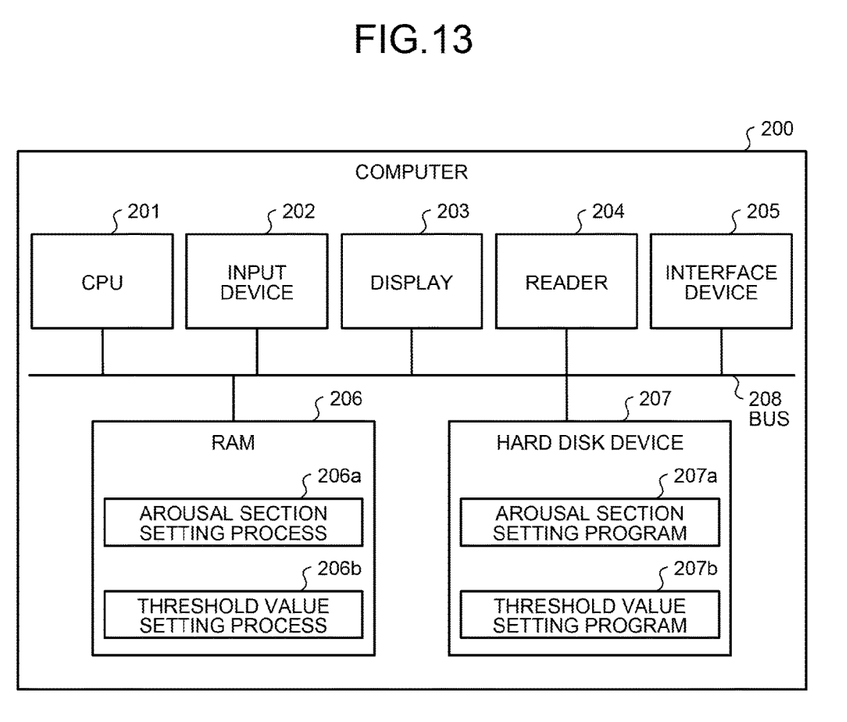
FIG. 13 is a diagram illustrating an example of a computer which executes an arousal level determination program.

Next, an example of a computer is described which executes an arousal level determination program. With the arousal level determination program, the same function as that of the arousal level determination device described in the above embodiment is realized. FIG. 13 is a diagram illustrating an example of a computer which executes the arousal level determination program.

As illustrated in FIG. 13, a computer 200 includes a CPU 201, an input device 202 and a display 203. The CPU 201 executes various processing. The input device 202 receives data input from a user. The computer 200 further includes a reader 204 and an interface device 205. The reader 204 reads a program or the like from a storage medium. The interface device 205 transmits and receives data to/from other computers via a network. The computer 200 further includes a RAM 206 which temporarily stores various information and a hard disk device 207. The respective devices 201 to 207 are connected to a bus 208.

The hard disk device 207 includes, for example, an arousal section setting program 207*a* and a threshold value setting program 207*b*. The CPU 201 reads the arousal section setting program 207*a* and the threshold value setting program 207*b*, and develops the programs on the RAM 206. The arousal section setting program 207*a* functions as an arousal section setting process 206*a*. The threshold value setting program 207*b* functions as a threshold value setting process 206*b*. The arousal section setting process 206*a* corresponds, for example, to the arousal section setting unit 140. The threshold value setting process 206*b* corresponds to the threshold value setting unit 150.

The arousal section setting program 207*a* and the threshold value setting program 207*b* are not necessarily stored in the hard disk device 207 initially. For example, each program is stored in "a portable physical medium" such as a flexible disk (FD), a CD-ROM, a DVD, a magneto-optical disk, and an IC card, to be inserted into the computer 200. Then, the computer 200 may read the arousal section setting program 207*a* and the threshold value setting program 207*b* from the medium to execute the programs.

According to an aspect of the present invention, it is possible to set, for each person, a threshold value for determining arousal levels.

All examples and conditional language provided herein are intended for pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable recording medium storing an arousal level determination program that causes a computer to execute a process comprising:
   first setting an arousal section including from a first time point when a subject whose heartbeat signal is detected has got on a vehicle whose driver is the subject to a second time point when a predetermined time has elapsed thereafter;
   determining whether an arousal level of the subject has moved toward arousal in a section which is temporally later than the arousal section, based on a biosignal that is the heartbeat signal detected from the subject;

when the arousal level of the subject has moved toward arousal in the section which is temporally later than the arousal section, updating the arousal section with a section in which the arousal level of the subject has moved toward arousal; and second setting a threshold value for determining whether the subject is in an arousal state, based on statistical values that are an average value and a standard deviation of the subject's arousal levels corresponding to the updated arousal section, wherein the updating includes specifying, as an arousal section, a section in which a subject's arousal level has moved toward arousal in comparison to the subject's arousal level in a section immediately after the subject has got on the vehicle, wherein the determining includes calculating, when calculating a relationship between a spectral density and a frequency, a spectral density with an autoregressive (AR) model.

2. The non-transitory computer-readable recording medium according to claim 1, the process further including:

calculating a difference value between an average interval of heartbeat intervals of the biosignal and heartbeat intervals of the biosignal corresponding to a certain section which is temporally later than the arousal section; and when the difference value is larger than a first predetermined value or smaller than a second predetermined value, executing a process which inhibits setting of the certain section as the arousal section.

3. The non-transitory computer-readable recording medium according to claim 1, wherein the second setting includes calculating an average value or a median value and a standard deviation of arousal levels included in the arousal section, and calculating the threshold value based on the average value or the median value and the standard deviation.

4. An arousal level determination device comprising:

a processor configured to execute a process including:

first setting an arousal section including from a first time point when a subject whose heartbeat signal is detected has got on a vehicle whose driver is the subject to a second time point when a predetermined time has elapsed thereafter, determines whether an arousal level of the subject has moved toward arousal in a section which is temporally later than the arousal section, based on a biosignal that is the heartbeat signal detected from the subject, and when the arousal level of the subject has moved toward arousal in the section which is temporally later than the arousal section, updating the arousal section with a section in which the arousal level of the subject has moved toward arousal; and second setting a threshold value for determining whether the subject is in an arousal state based on statistical values that are an average value and a standard deviation of arousal levels corresponding to the arousal section updated at the first setting, wherein the updating includes specifying, as an arousal section, a section in which a subject's arousal level has moved toward arousal in comparison to the subject's arousal level in a section immediately after the subject has got on the vehicle, wherein the determining includes calculating, when calculating a relationship between a spectral density and a frequency, a spectral density with an autoregressive (AR) model.

5. The arousal level determination device according to claim 4, wherein the first setting includes calculating a difference value between an average interval of heartbeat intervals of the biosignal and heartbeat intervals of the biosignal corresponding to a certain section which is temporally later than the arousal section, and when the difference value is larger than a first predetermined value or smaller than a second predetermined value, the first setting further includes executing a process which inhibits setting of the certain section as the arousal section.

6. The arousal level determination device according to claim 4, wherein the second setting include calculating an average value or a median value and a standard deviation of arousal levels included in the arousal section, and calculating the threshold value based on the average value or the median value and the standard deviation.

* * * * *